(12) United States Patent
Benabid et al.

(10) Patent No.: US 7,991,481 B2
(45) Date of Patent: Aug. 2, 2011

(54) MULTIPLE ELECTRODE LEAD AND A SYSTEM FOR DEEP ELECTRICAL NEUROSTIMULATION INCLUDING SUCH A LEAD

(75) Inventors: Alim Louis Benabid, Meylan (FR); Fabien Sauter-Starace, Seyssinet-Pariset (FR); Patrice Caillat, Grenoble (FR)

(73) Assignee: Commissariat A L'Energie Atomique, Paris (FR)

( * ) Notice: Subject to any disclaimer, the term of this patent is extended or adjusted under 35 U.S.C. 154(b) by 421 days.

(21) Appl. No.: 12/216,305

(22) Filed: Jul. 2, 2008

(65) Prior Publication Data

US 2009/0012593 A1 Jan. 8, 2009

(30) Foreign Application Priority Data

Jul. 3, 2007 (FR) ...................................... 07 04804

(51) Int. Cl.
*A61N 1/05* (2006.01)
(52) U.S. Cl. ....................................................... 607/116
(58) Field of Classification Search .................. 607/116, 607/117
See application file for complete search history.

(56) References Cited

U.S. PATENT DOCUMENTS

| | | | | |
|---|---|---|---|---|
| 6,066,165 A * | 5/2000 | Racz | ............................. | 607/117 |
| 6,512,958 B1 | 1/2003 | Swoyer et al. | | |
| 6,529,774 B1 * | 3/2003 | Greene | ......................... | 600/545 |
| 7,006,859 B1 * | 2/2006 | Osorio et al. | ................. | 600/378 |
| 7,162,308 B2 | 1/2007 | O'Brien et al. | | |
| 7,676,273 B2 * | 3/2010 | Goetz et al. | ..................... | 607/62 |
| 2005/0222647 A1 | 10/2005 | Wahlstrand et al. | | |
| 2006/0041295 A1 | 2/2006 | Osypka | | |
| 2007/0088404 A1 | 4/2007 | Wyler et al. | | |
| 2007/0150039 A1 * | 6/2007 | Leigh et al. | ................... | 607/152 |
| 2008/0195187 A1 * | 8/2008 | Li et al. | ......................... | 607/116 |
| 2009/0270957 A1 * | 10/2009 | Pianca et al. | ................. | 607/116 |

FOREIGN PATENT DOCUMENTS

FR  2 912 921  8/2008

OTHER PUBLICATIONS

P. Krack et al., "Stimulation of subthalamic nucleus alleviates tremor in Parkinson's disease", *Research letters*, vol. 350, Dec. 6, 1997, pp. 1675.
A. Benabid et al., "Chronic VIM Thalamic Stimulation in Parkinson's Disease, Essential Tremor and Extra-Pyramidal Dyskinesias", *Acta Neurochir*, (1993) [Suppl] 58: pp. 39-44.
A. Takaki et al., "Feeding suppression elicited by electrical and chemical stimulations of monkey hypothalamus", *Am. J. Physiol.* 262 (Regulatory Integrative Comp. Physiol. 31) R586-R594, 1992.

(Continued)

*Primary Examiner* — Kennedy J Schaetzle
(74) *Attorney, Agent, or Firm* — Clark & Brody

(57) ABSTRACT

A lead for deep electrical neurostimulation comprising a rod of biocompatible material and a blade, also of biocompatible material, secured to one end of the rod and in alignment therewith. The blade presents two main faces and a plurality of electrodes disposed on at least one of the two main faces in a two-dimensional configuration. The electrodes are connected to conductor elements disposed inside or on a surface of said rod. A deep electrical neurostimulation system comprising an electrical pulse generator connected to at least one lead of the above-described type is also disclosed.

9 Claims, 3 Drawing Sheets

OTHER PUBLICATIONS

K. Sano et al., "Results of stimulation and destruction of the posterior hypothalamus in man", *J. Neurosurg.*, vol. 33, Dec. 1970, pp. 689-707.

C. Bielajew et al., "Factors that contribute to the reduced weight gain following chronic ventromedial hypothalamic stimulation", *Behavioral Brain Research* 62 (1994) pp. 143-148.

F. Brown, M.D. et al., "Changes in food intake with electrical stimulation of the ventromedial hypothalamus in dogs", *J Neurosurg* 60: 1253-1257, 1984.

K. Lee et al., "Biocompatible benzocyclobutene (BCB)-based neural implants with micro-fluidic channel", *Biosensor and Bioelectronics* 20 (2004) 404-407.

H. Mayberg et al., "Deep Brain Stimulation for Treatment-Resistant Depression", *Neuron*, vol. 45, 651-660, Mar. 3, 2005.

* cited by examiner

MULTIPLE ELECTRODE LEAD AND A SYSTEM FOR DEEP ELECTRICAL NEUROSTIMULATION INCLUDING SUCH A LEAD

The invention relates to a lead for deep electrical neurostimulation, and more particularly for deep brain electrostimulation. The invention also relates to a system for deep electrical neurostimulation and including at least one such lead.

BACKGROUND OF THE INVENTION

Deep brain stimulation is a therapeutic technique comprising implanting a medical appliance known as a brain stimulator that serves to send electrical pulses to specific regions of the brain. For example, stimulation of the nuclei of the thalamus or of the hypothalamus can be used for treating motor disorders such as tremor, caused in particular by Parkinson's syndrome; in this context, reference can be made to the following articles:

P. Krack, P. Pollak, P. Limousin, A. Benzzaous, A. L. Benabid, The Lancet, Vol. 350, Dec. 6, 1977; and A. L. Benadid et al., Acta Neurochirurgica suppl., Vol. 58, pp. 39-44, 1993.

It has also been envisaged to stimulate the posterior hypothalamic nucleus for treating cluster headaches, periaqueductal gray matter for attenuating pain, and the ventromedial hypothalamus for treating certain kinds of obesity; in this respect, reference can be made to the following articles:

A. Takaki, S. Aou, Y. Oomura, E. Okada, T. Hori, "Feeding suppression elicited by electrical and chemical stimulation of monkey hypothalamus", Am. J. Physiol. 262 (Regulatory Integrative Comp. Physiol. 31) R586-R594, 1992.

K. Sanyo, Y. Mayanagi, H. Sekino, M. Ogashiwa, et al., "Results of stimulation and destruction of the posterior hypothalamus in man", J. Neureosurg 33, Dec. 1970, pop. 689-707.

C. Bielajew, J. Stenger, D. Schindler, "Factors that contribute to reduce weight gain following chronic ventromedial stimulation", Behav. Brain Res. 62 (1994), pp. 143-156.

F. Brown, R. Fessler, J. Rachlin, S. Mullan, "Changes in food intake with electrical stimulation of the ventromedial hypothalamus in dogs", J. Neurosurg. 60, pp. 1253-1257 (1984).

Recently, a study has shown that electrical stimulation of the subgenual cingulate cortex, and more precisely of Brodmann area 25 (CG25) can be used for treating particularly severe and treatment-resistant forms of clinical depression [H. S. Mayberg et al., "Deep brain stimulation for treatment-resistant depression", Neuron, Vol. 45, pp. 651-660, Mar. 3, 2005]. The stimulation method recommended is stimulation of the CG25 subgenual cortex by direct application, between the hemispheres, using electrodes presenting surfaces similar to those used for stimulating premotor cortexes in indications for refractory pain.

In any event, deep brain stimulation involves inserting a flexible lead into the patient's skull under guidance from a cannula and/or a rigid stylet, until the tip of said lead reaches the region of the brain that is to be stimulated. Close to its tip, the lead has electrodes (generally four electrodes) that are connected via a subcutaneous cable to a pulse generator appliance that is implanted under the patient's skin like a conventional cardiac pacemaker. The cannula and/or the stylet are extracted from the patient's skull after being used for inserting the lead, and the lead is then left in place for a duration that may be as long as several years.

A more detailed description of the procedure for implanting a lead for deep brain stimulation is given by the following document: "Medtronic—DBS™ lead kit for deep brain stimulation 3387 3389—Implant manual" from the supplier Medtronic Inc., downloadable from the following Internet site: http://www.medtronic.com/physician/activa/downloadablefiles/197928_b_006.pdf Leads for deep electrical neurostimulation of conventional type are described for example in the above-mentioned document from the supplier Medtronic, and also in document U.S. Pat. No. 6,512,958.

The rectilinear shape of the lead is required by the need to make insertion thereof as little traumatic as possible for the patient. However, that has the drawback of allowing only a very small region of brain tissue to be stimulated, whereas in order to obtain more effective treatment it would be desirable to be able to act on a target of larger volume. Implanting a plurality of leads directed at distinct points of a common target region of relatively large volume is indeed possible, but that multiplies the risks and the side effects of the surgery.

OBJECTS AND SUMMARY OF THE INVENTION

An object of the invention is thus to provide a lead for deep electrical neurostimulation making it possible, at least in the context of certain applications, such as stimulating the CG25 region, to obtain more effective treatment, while minimizing the risks and the side effects of such treatment.

According to the invention, this object is achieved by a lead for deep electrical neurostimulation, the lead comprising: a rod of biocompatible material; and a blade, also of biocompatible material, secured to one end of said rod and in alignment therewith; in which said blade presents two main faces and a plurality of electrodes disposed on at least one of said two main faces in a two-dimensional configuration, said electrodes being connected to conductor elements disposed inside or on a surface of said rod.

In particular embodiments of the invention:

Said blade may present a plurality of electrodes disposed on its two opposite main faces.

The number of electrodes placed on said or each main face of said blade may lie in the range 1 to 40 and preferably in the range 5 to 20.

Said rod may be substantially rectilinear.

Said rod and said blade may be made, at least in part, out of a biocompatible material selected from: silicones; siloxanes; polyurethane; polyvinyl chloride; benzocyclobutene (BCB); polyimides; and parylen.

Said rod and said blade may be made as a single piece.

Said lead may present a total length lying in the range 4 centimeters (cm) to 10 cm, and preferably in the range 5 cm to 8 cm.

Said lead may present a substantially planar shape, with a thickness lying in the range 25 micrometers (µm) to 3 millimeters (mm), and preferably in the range 50 µm to 2 mm.

Said main faces of the blade may present an area lying in the range 10 square millimeters ($mm^2$) to 500 $mm^2$, and preferably in the range 20 $mm^2$ to 450 $mm^2$.

Said blade may present a sickle shape, an elliptical shape, or a shape that matches the outline of a CG25 zone of a human brain.

At least said rod may present a hollow section with a lumen extending longitudinally therein, in which case said lead may include a rigid stylet inserted removably within said lumen.

Said rod may present, at rest, a shape that is not rectilinear and that is capable of straightening in reversible manner when said stylet is inserted therein and of returning to its non-rectilinear shape when the stylet is withdrawn.

Said blade may be hollow and capable of stretching reversibly during insertion of said stylet so as to be capable of returning to its original shape when the stylet is withdrawn.

Said lead may include longitudinal stiffener beams incorporated in said rod. Said longitudinal stiffener beams may be made of a material selected from non-magnetic metals and alloys and carbon fibers.

Said electrodes may present a covering of electrically-conductive carbon nanotubes, and more particularly multi-walled nanotubes, preferably with ramifications, covering silicone pellets fitted onto the surfaces of said electrodes.

The invention also relates to a deep electrical neurostimulation system comprising: an electrical pulse generator for deep electrical neurostimulation; and at least one lead as described above, having its electrodes electrically connected to said electrical pulse generator.

BRIEF DESCRIPTION OF THE DRAWINGS

Other characteristics, details, and advantages of the invention appear on reading the following description made with reference to the accompanying drawings given by way of example and showing, respectively.

MORE DETAILED DESCRIPTION

The lead 1 of the invention essentially comprises two portions: a substantially rectilinear rod 10 and a blade 20 in the form of a sickle or kidney bean, secured to a so-called "distal" end of said rod 10 and in alignment therewith, so as to constitute an extension. Both the rod 10 and the blade 20 are made of biocompatible material, preferably a relatively flexible material such as silicone, siloxane, polyurethane, polyvinyl chloride, benzocyclobutene (BCB), polyimide, and parylen. The rod 10 and the blade 20 are preferably made as a single piece, but that is not essential.

Figure 3:
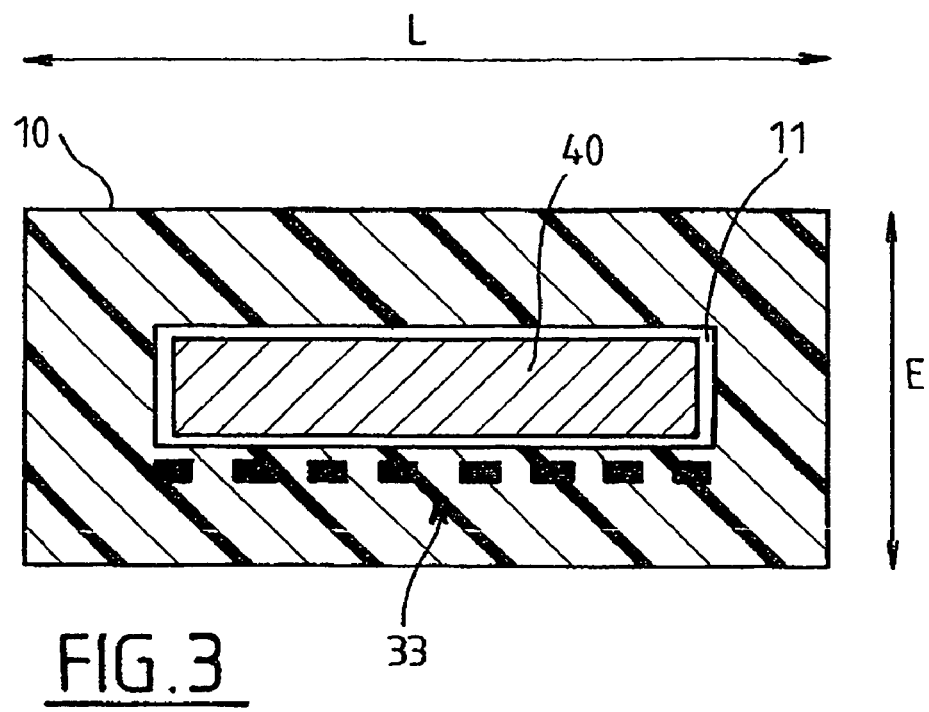
FIG. 3, a cross-section view on line III-III of a lead in said first embodiment of the invention.
Figure 4:
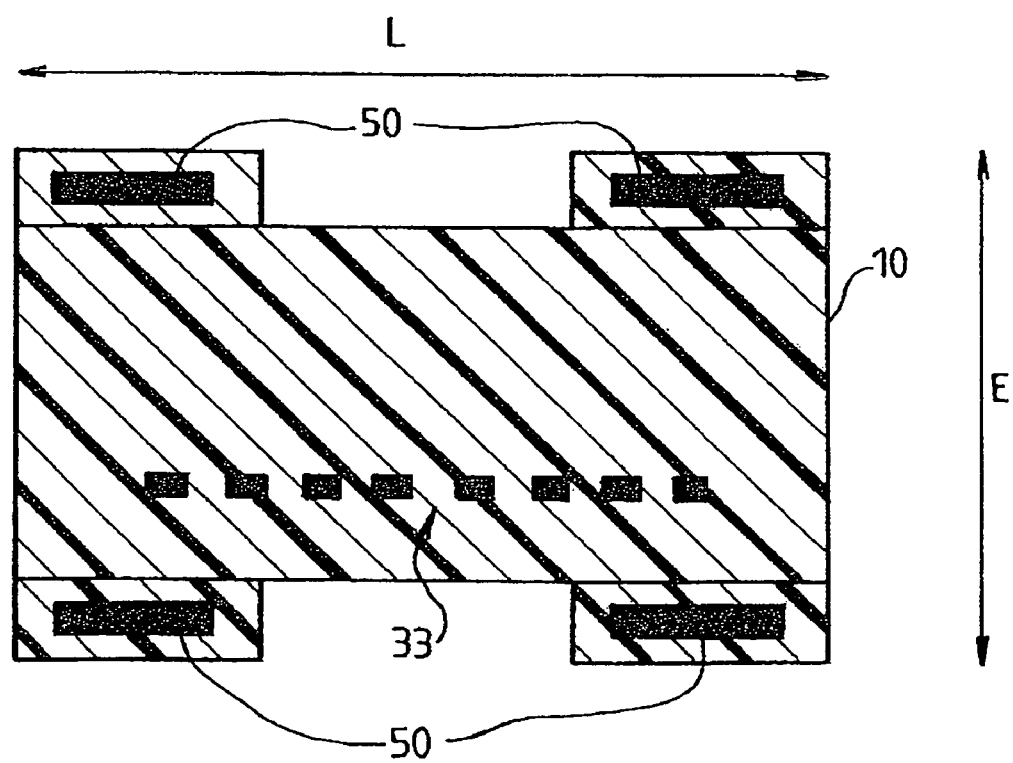
FIG. 4, a cross-section view of a lead in a second embodiment of the invention.

The lead 1 presents a structure that is substantially planar. The rod 10 presents a section that is at least approximately rectangular, as shown in FIGS. 3 and 4, having thickness E generally lying in the range 25 μm to 3 mm, and preferably lying in the range 50 μm to 2 mm, and a width L generally lying in the range 10 mm to 40 mm, and preferably in the range 15 mm to 30 mm. In a variant, the rod 10 may also be substantially cylindrical in shape, having a radius generally lying in the range 0.5 mm to 2 mm. The rod 10 may be situated in the middle of the blade 20 as shown in the figures, or else on one edge thereof, depending on the shape of the zone that is to be stimulated and depending on rigidity constraints during insertion.

Figure 1:
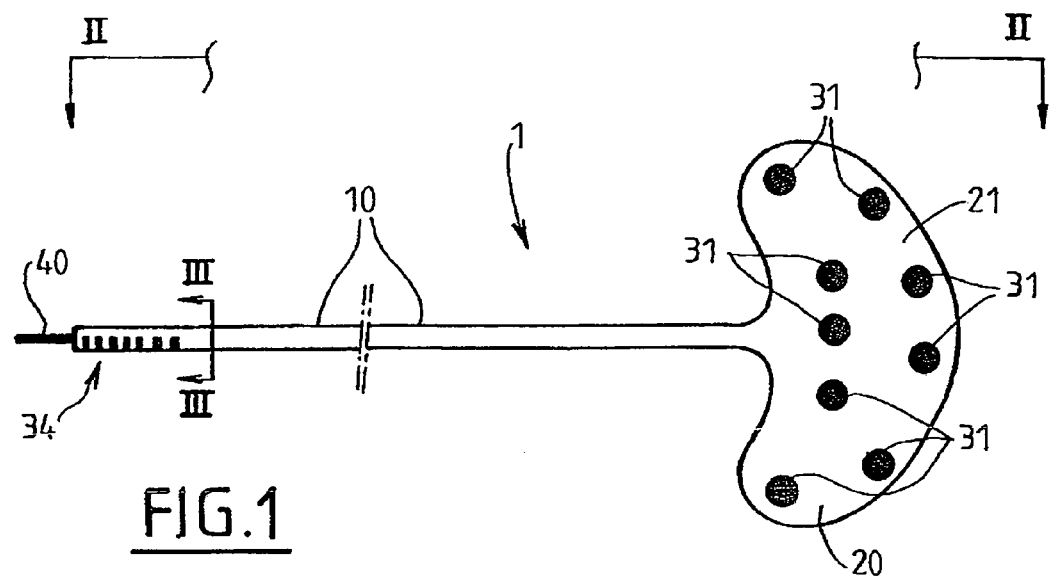
FIG. 1, a plan view of a lead of the invention.
Figure 2:
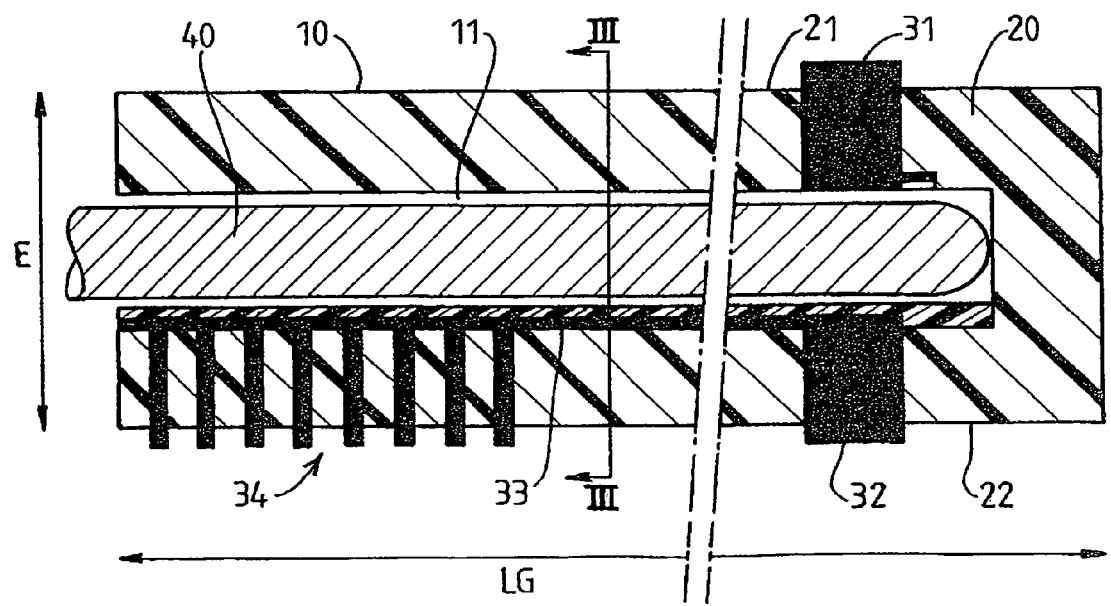
FIG. 2, a longitudinal section view on line II-II of a lead in a first embodiment of the invention.
Figure 5:
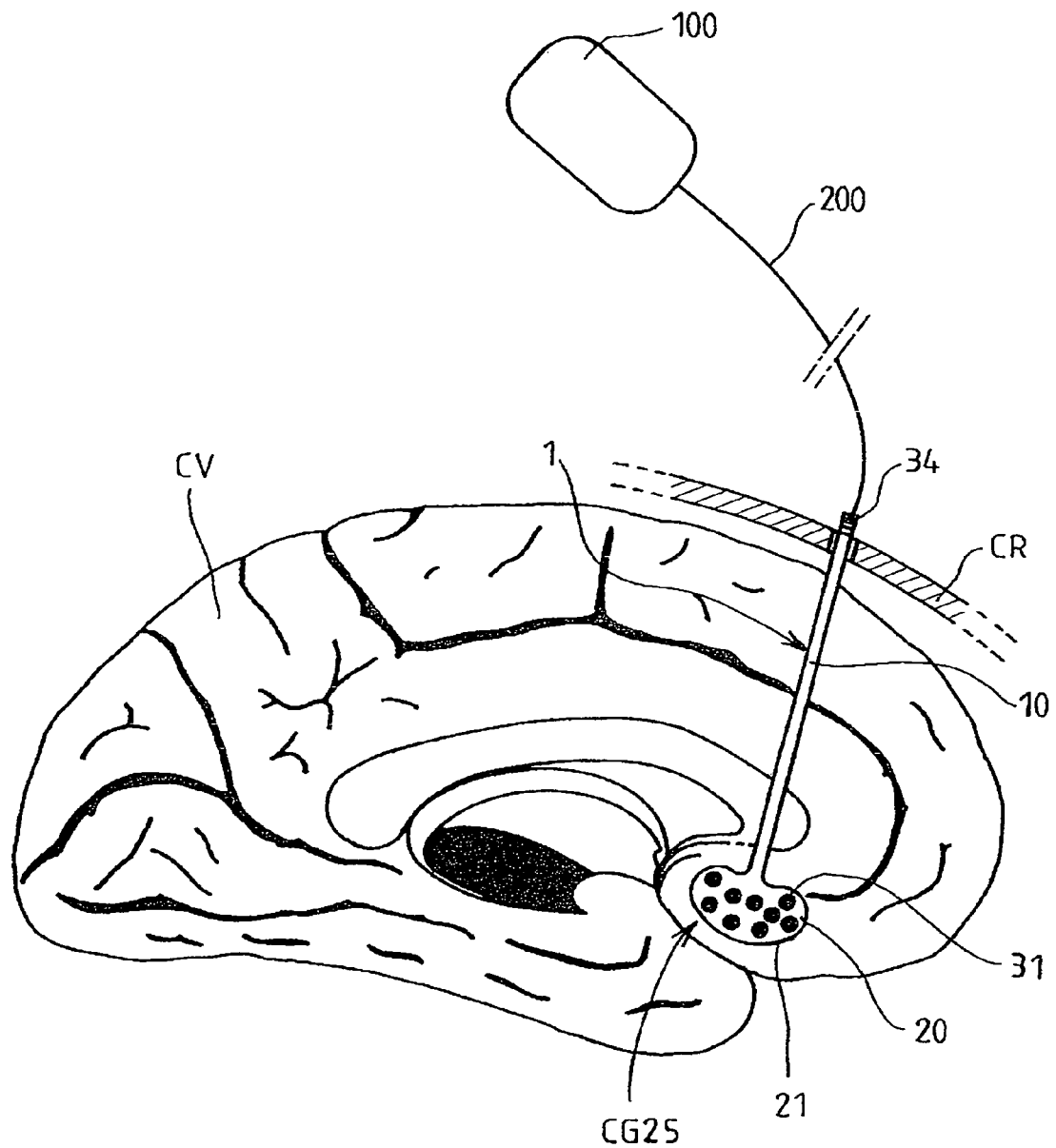
FIG. 5, a diagram showing the principle of a deep electric neurostimulation system including a lead of the invention implanted in the brain of a patient in order to stimulate the CG25 region of the patient's subgenual cingulate cortex.

The blade 20 also presents a structure that is substantially planar, having thickness of the same order as magnitude as that of the rod 10, and preferably having the same thickness. The blade presents two opposite main faces 21 and 22 that, in the example shown in FIGS. 1 and 5, are sickle shaped, with an area lying approximately in the range 10 mm$^2$ to 750 mm$^2$, and preferably in the range 100 mm$^2$ to 450 mm$^2$. The sickle or kidney bean shape is selected because it corresponds approximately to the shape of the CG25 area that is to be stimulated. In a variant, it is possible to select a shape that is more complex, fitting more precisely to the outline of the CG25 area, or conversely a shape that is simpler, being elliptical or circular. Different shapes may be provided, in particular for stimulating other zones of the brain. In general, it is advantageous for the blade 20 to extend over the entire surface of the zone that is to be stimulated, or even further.

The length LG of the lead 1 preferably lies in the range 3 cm to 8 cm. This length must be sufficient to reach the target tissue for stimulation, e.g. the CG25 region of the human brain, without excessively projecting beyond the surface of the patient's body.

Electrodes 31, 32 project from the two opposite main faces 21 and 22 of the blade 20. These electrodes are made of a biocompatible conductive material such as platinum and they are disposed in a two-dimensional configuration. By way of example, FIG. 1 shows a lead 1 in which the blade 20 presents nine electrodes on each of its main faces, the electrodes being disposed in a pattern that enables the CG25 area to be stimulated approximately uniformly. The number of electrodes on each main face 21, 22 may for example lie in the range 1 to 40, and preferably in the range 5 to 20.

The dimensions of the electrodes 31, 32 are determined as a function of the intended stimulation current, it being understood that it is not desirable to exceed a charge density of 30 micro coulombs per square centimeter (μC/cm$^2$) per pulse.

In a variant, only one of the main faces of the blade 20 needs be provided with electrodes, so that the target tissue is electrically stimulated only unilaterally. Bilateral electrostimulation can also be obtained by making use of two leads of this type placed back to back.

The electrodes 31, 32 are connected to conductor elements 33 that extend longitudinally along the rod 10 as far as external electrical contacts 34 situated at the so-called "proximal" end of the rod, remote from the blade 20. As shown in FIG. 5, when the lead 1 is implanted in the brain CV of a patient, the external electrical contacts project outside the cranium CR, and enable the electrodes 31, 32 to be electrically connected to an electrical pulse generator 100 for deep electrical neurostimulation via a subcutaneous cable 200.

The conductor elements 33 may be disposed inside the rod 10 or on its surface; however, if they are on the surface they must be covered in a layer that is electrically insulating and passivating.

The lead 1 of the invention, and in particular its rod 10, must be sufficiently flexible to avoid giving rise to internal lesions when it is permanently implanted, e.g. in the brain of a patient. Simultaneously, in order to be inserted it must present sufficient stiffness.

In known manner, these contradictory requirements are solved by using a lead 1, or at least a rod 10, that presents a hollow section with a longitudinal lumen 11 in which it is possible to insert removably a stiffener stylet 40 that is designed to be extracted from the lead 1 after it has been introduced into the body of a patient.

In a variant of the invention, the rod 10 may be preformed to present a non-rectilinear shape. Such a rod straightens out reversibly when the stylet 40 is inserted, thus making it easier to implant; thereafter, when the stylet is withdrawn it returns to its original non-rectilinear shape. This makes it possible to reach zones of the brain that would otherwise be difficult to access, and minimizes lesions to the parenchyma caused by inserting the lead.

It is also possible to make a lead presenting a blade 20 that is hollow and that preferably includes longitudinal notches. When the stylet 40 bears against the distal end of the lead, such a blade stretches, becoming longer and narrower. The lead then becomes almost rectilinear in shape, thereby minimizing the size of the incision that needs to be made in the cranium in order to insert it, and also minimizing lesions to the parenchyma caused by said insertion. When the stylet is withdrawn, the blade 20 returns to its original shape in order to stimulate the target region of the brain effectively.

Cerebral stimulation leads of shape that is temporarily modified by inserting a stiffener stylet are described in greater detail in patent application FR 07/01353 filed on Feb. 26, 2007 by the present Applicant.

In some circumstances, it can be preferable to use a lead 1 that is itself provided with a certain amount of stiffness, but that has a covering that is relatively flexible. This can be achieved by stiffening a lead that is made mainly out of flexible material by incorporating longitudinal beams 50, e.g. made of tantalum or of titanium, or of any other metal that is biocompatible and compatible with magnetic resonance imaging (MRI), or out of carbon fibers. The beams 50 are preferably far away from the bending axis of the rod 10, which amounts to increasing the stiffness of the beams for given volume.

In the embodiment of FIG. 4, the beams 50 stiffen the lead 1 sufficiently to enable it to be inserted without a stylet 40 being necessary; consequently, the lead has a solid section, without any lumen. It is also possible to envisage an intermediate embodiment in which the beams 50 do not provide sufficient stiffness, with a removable stylet 40 being used for inserting the lead, as in the embodiment of FIG. 3.

From a technical point of view, leads of the invention can be obtained using various fabrication methods.

For leads having a thickness greater than 100 μm and up to a few millimeters, in order to fabricate the electrodes 31, 32, the conductor elements 33, and the external electrical contacts 34, it is preferable to use steps of photolithography and of etching a metal on an elastomer of the siloxane type, or steps of depositing conductive inks by depositing nanopowders, followed by a laser sintering operation that enables good electrical conduction to be achieved, these steps being followed by passivation with photosensitive silicone or parylen locally opened by plasma or laser etching.

For leads of thickness lying in the range 10 μm to 100 μm approximately, the starting material is an optionally photosensitive polymer (shape obtained by lithography or by plasma etching), such as a polyimide or benzocyclobutene (BCB), deposited by centrifuging, and having two-dimensional conductor patterns thereon constituting the electrodes 31, 32, the conductor elements 33, and the external electrical contacts 34 which patterns are made by photolithography or likewise by depositing conductive inks or by depositing nanopowders. The first method (lithography) enables resolutions to be achieved that are of micrometer order, whereas the other methods are restricted to patterns greater than 10 μm. Passivation is obtained by depositing a second layer of the same polymer. A hollow section can be obtained using sacrificial layers, as described in the article by Kee Keun Lee, Jiping He, Ryan, Clement, Stephen Massia, and Bruce Kim, published in the journal "Biosensors and bioelectronics", No. 20, pp. 404 to 407, 2004, or else by sealing after photo-polymerization. It is with such extremely fine leads that it is the most advantageous to make use of reinforcing beams 50.

In any event, the conductor elements 33 can be made of metal, indium and tin oxide (ITO), or graphite, and they may be textured by methods derived from semiconductor or printed circuit technology.

In order to increase the biocompatibility of the stimulation and/or recording electrodes, it is possible to add thin silicon pellets coated in carbon nanotubes. The electrical properties of carbon nanotubes (multiple walls, with or without ramification) produce a very significant increase in the signal-to-noise ratio by reducing the impedance of the electrode (which property is associated with increasing its developed surface area). Such performance is desirable for an electrode that records cortical activity in the stimulation zone like an electrocorticogram (analogous to an electroencephalogram, but made on the cortex).

In stimulation, electrodes including carbon nanotubes also present advantages. The electrochemical characterizations of such electrodes show that the quantity of charge that can be injected is much greater than that from a titanium nitride electrode or a platinum electrode (e.g. characterization performed by CEA/Leti: where the capacitance per unit area of electrodes with carbon nanotubes has been measured at $1.3 \times 10^{-2}$ farads per square centimeter ($F/cm^2$) as compared with $5.10 \times 10^{-4}$ $F/cm^2$ for the same electrodes without nanotubes. The use of carbon nanotubes thus provides a significant advantage for stimulation electrodes. In addition, document U.S. Pat. No. 7,162,308 describes the advantages of growing carbon nanotubes out of biocompatibility material.

The use of a lead of the invention to treat certain forms of clinical depression is illustrated in FIG. 5. In these forms of depression, region 25 of the subgenual cingulate cortex, CG25, is hyperactive, and this hyperactivity can be moderated by chronic electrical stimulation. Each hemisphere of the brain CV has its own CG25 region, adjacent to the longitudinal fissure of the cerebrum (coronal section plane of the figure). In general, it is desirable to stimulate the regions in both hemispheres, however unilateral stimulation may be preferred in certain special circumstances.

A lead 1 of the invention can be inserted into the skull of a patient via an opening of appropriate shape made through the cranium CR, the blade 20 sliding in the plane of the longitudinal fissure.

More precisely, the patient is positioned on a stereotaxic frame, a stereotaxic robot also being positioned on said frame to determine on the scalp the site for the cutaneous incision, and the center of the right parasagittal trepan that is to be made to approach the longitudinal fissure of the cerebrum, under an operating microscope. Thereafter, a cutaneous incision is made parallel to the corona suture, thus making it more attractive than a parasagittal incision, which would run the risk of projecting too far beyond the hair line. With the scalp retracted, craniotomy is performed using a trepan having a diameter of 3 cm or 5 cm, on the non-dominant side of the patient, thus generally on the right-hand side if the patient is right-handed, tangentially to the midline. The dura-mater is incised along a diameter parallel to the midline, and two radial slits are formed towards the midline so as to lead to the longitudinal fissure of the cerebrum. This is carefully separated from the falx of cerebrum by sectioning adhesions of the arachnoidea to the level of the base of the anterior stage, going towards the most posterior, subgenual portion of the mediobasal frontal cortex. The stereotaxic installation makes it possible to perform radiological monitoring during the operation to ensure that positioning is correct relative to the determined target.

Thereafter, the lead 1 is advanced inside said longitudinal fissure, where appropriate with the help of a stiffener stylet 40, until the blade 20 carrying the electrodes 31, 32 reaches the CG25 region that is to be stimulated. After the stylet 40 has been withdrawn, X-ray inspection is performed and the dura-mater is sutured, the piece of bone is put back into place and secured to the scalp by non-resorbable stitches, allowing the cable to the electrodes to extend outwards via the saw cut of the trepan. The distal ends are left under the periosteum in the same manner as for intra-parenchyme electrodes.

On the third day after implanting the electrodes, a new MRI is performed to monitor the positions of the electrodes and to verify that there are no bleeding complications.

Under general anesthesia, six days after implantation, an electrical pulse generator 100 for deep electrical neurostimulation is implanted under the skin of the patient in the right subclavicular region, and is connected to the external electrical contacts 34 of the lead via a double extender 200 running from the head to the collar bone through successive cutaneous tunnels.

In a variant, two leads 1, each having electrodes on only one main face of the blade 20, may be placed back to back and connected to the same pulse generator 100, or to two individual generators.

Although the invention is described above with reference to its use for treating clinical depression by stimulating region 25 of the subgenual cingulate cortex (CG25), the invention can be applied more generally to deep electrical neurostimulation of other regions of the brain, or indeed of other tissues, such as the spinal cord.

What is claimed is:

1. A lead for deep electrical neurostimulation, the lead comprising:
   a rod of biocompatible material, having a stiffness which is sufficient for allowing its insertion into a brain of a patient; and
   a blade, also of biocompatible material, secured to one end of said rod and in alignment therewith;
   in which said blade presents two main faces and a plurality of electrodes disposed on at least one of said two main faces in a two-dimensional configuration, said electrodes being connected to conductor elements disposed inside or on a surface of said rod;
   wherein said lead presents a total length lying in the range 4 cm to 10 cm.

2. A lead according to claim 1, presenting a total length lying in the range 5 cm to 8 cm.

3. A lead for deep electrical neurostimulation, the lead comprising:
   a rod of biocompatible material, having a stiffness which is sufficient for allowing its insertion into a brain of a patient; and
   a blade, also of biocompatible material, secured to one end of said rod and in alignment therewith;
   in which said blade presents two main faces and a plurality of electrodes disposed on at least one of said two main faces in a two-dimensional configuration, said electrodes being connected to conductor elements disposed inside or on a surface of said rod;
   wherein said lead presents a substantially planar shape, with a thickness lying in the range 25 µm to 3 mm.

4. A lead according to claim 3, presenting a thickness lying in the range 50 µm to 2 mm.

5. A lead for deep electrical neurostimulation, the lead comprising:
   a rod of biocompatible material, having a stiffness which is sufficient for allowing its insertion into a brain of a patient; and
   a blade, also of biocompatible material, secured to one end of said rod and in alignment therewith;
   in which said blade presents two main faces and a plurality of electrodes disposed on at least one of said two main faces in a two-dimensional configuration, said electrodes being connected to conductor elements disposed inside or on a surface of said rod;
   wherein said main faces of the blade present an area lying in the range 10 mm$^2$ to 500 mm$^2$.

6. A lead according to claim 5, wherein said main faces of the blade present an area lying in the range 20 mm$^2$ to 450 mm$^2$.

7. A lead for deep electrical neurostimulation, the lead comprising:
   a rod of biocompatible material, having a stiffness which is sufficient for allowing its insertion into a brain of a patient; and
   a blade, also of biocompatible material, secured to one end of said rod and in alignment therewith;
   in which said blade presents two main faces and a plurality of electrodes disposed on at least one of said two main faces in a two-dimensional configuration, said electrodes being connected to conductor elements disposed inside or on a surface of said rod;
   wherein said blade presents a sickle shape, an elliptical shape, or a shape that matches the outline of a CG25 zone of a human brain.

8. A lead for deep electrical neurostimulation, the lead comprising:
   a rod of biocompatible material, having a stiffness which is sufficient for allowing its insertion into a brain of a patient; and
   a blade, also of biocompatible material, secured to one end of said rod and in alignment therewith;
   in which said blade presents two main faces and a plurality of electrodes disposed on at least one of said two main faces in a two-dimensional configuration, said electrodes being connected to conductor elements disposed inside or on a surface of said rod;
   in which said electrodes present a covering of electrically-conductive multi-wall carbon nanotubes covering pellets of silicon fitted onto the surface of said electrodes.

9. A deep electrical neurostimulation system comprising:
   an electrical pulse generator for deep electrical neurostimulation; and
   at least one lead for deep electrical neurostimulation having its electrodes electrically connected to said electrical pulse generator,
   wherein the lead comprises:
   a rod of biocompatible material, having a stiffness which is sufficient for allowing its insertion into a brain of a patient; and
   a blade, also of biocompatible material, secured to one end of said rod and in alignment therewith, said blade having two main faces and a plurality of electrodes disposed on at least one of said two main faces in a two-dimensional configuration, said electrodes being connected to conductor elements disposed inside or on a surface of said rod; and
   wherein said electrical pulse generator is configured to generate electrical impulsion adapted for treating clinical depression by stimulating a CG25 zone of a human brain.

* * * * *